United States Patent [19]

Kamishita et al.

[11] Patent Number: 5,064,122
[45] Date of Patent: Nov. 12, 1991

[54] DISPOSABLE NOZZLE ADAPTER FOR INTRANASAL SPRAY CONTAINERS

[75] Inventors: Takuzo Kamishita, Takatsuki; Toshiaki Takagi, Toyama, both of Japan

[73] Assignee: Toko Yakuhin Kogyo Kabushiki Kaisha, Osaka, Japan

[21] Appl. No.: 565,234

[22] Filed: Aug. 10, 1990

[30] Foreign Application Priority Data

Aug. 11, 1989 [JP] Japan .................................. 1-208628
Oct. 24, 1989 [JP] Japan .................................. 1-276630

[51] Int. Cl.$^5$ ............................................... B05B 1/34
[52] U.S. Cl. ................................. 239/396; 239/491; 239/496; 239/497
[58] Field of Search ............... 239/390, 391, 396, 490, 239/491, 494, 496, 497; 222/402.1

[56] References Cited

U.S. PATENT DOCUMENTS

| | | | |
|---|---|---|---|
| 2,668,084 | 2/1954 | Saxton | 239/491 |
| 3,140,052 | 7/1964 | McCuiston | 239/490 X |
| 3,416,737 | 12/1968 | Venus, Jr. | 239/490 X |
| 3,669,359 | 6/1972 | Focht | 239/491 |
| 3,724,763 | 4/1973 | Braun | 239/490 |
| 3,762,409 | 10/1973 | Lester | 239/424 X |
| 4,161,281 | 7/1979 | Erb et al. | 239/496 X |
| 4,187,985 | 2/1980 | Goth | 239/491 X |
| 4,801,093 | 1/1989 | Brunet et al. | 239/490 |

FOREIGN PATENT DOCUMENTS

| | | |
|---|---|---|
| 3038477 | 5/1979 | Australia . |
| 0131501 | 1/1985 | European Pat. Off. . |
| 2443879 | 7/1980 | France . |
| 13349 | of 1912 | United Kingdom ............... 239/490 |

*Primary Examiner*—Andres Kashnikow
*Assistant Examiner*—William Grant
*Attorney, Agent, or Firm*—Wegner, Cantor, Mueller & Player

[57] ABSTRACT

A disposable nozzle adapter for intranasal administration of a viscous medical solution in combination with a spray container, which comprises a cylindrical body, a rod arranged in the body, and a nozzle tip. The body has a cylindrical chamber and a central bore communicated with the chamber through a channel for attachment of the spray container. The rod is provided on its one end at the least with a small-sized portion and middle-sized portion. The nozzle tip has a top wall and a cylindrical portion extending therefrom, the top wall being provided with a central spray opening including a tapered recess, and swirl grooves extending outwardly from the tapered recess to the inner surface of the cylindrical portion. The swirl grooves have a cross-sectional area increasing outwardly and its cross-sectional area is 0.03 to 0.08 mm$^2$ at the minimum. The nozzle tip is fitted in the opening of the chamber of the body and engaged with the middle-sized portion of the rod to form an annular channel surrounding the small-sized portion of the rod and being communicated with the grooves.

5 Claims, 2 Drawing Sheets

Fig. 1
Fig. 2
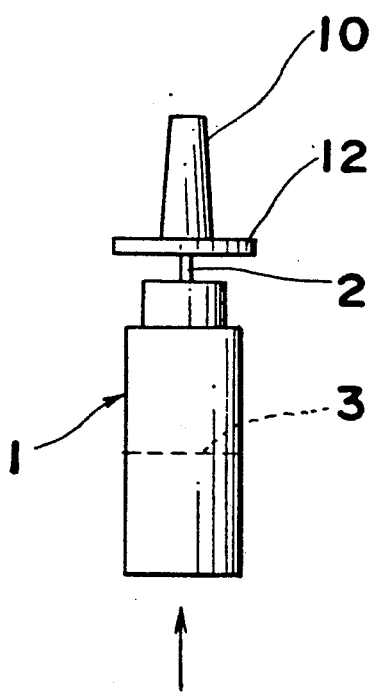
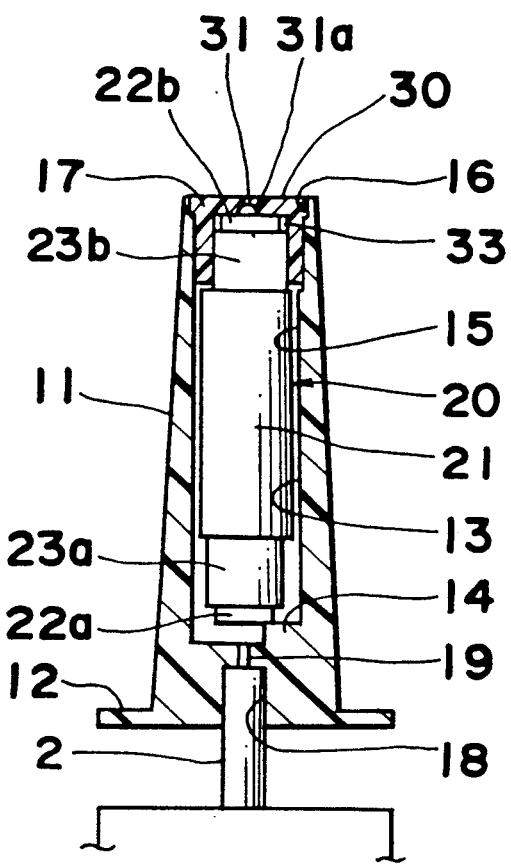
Fig. 4
Fig. 5
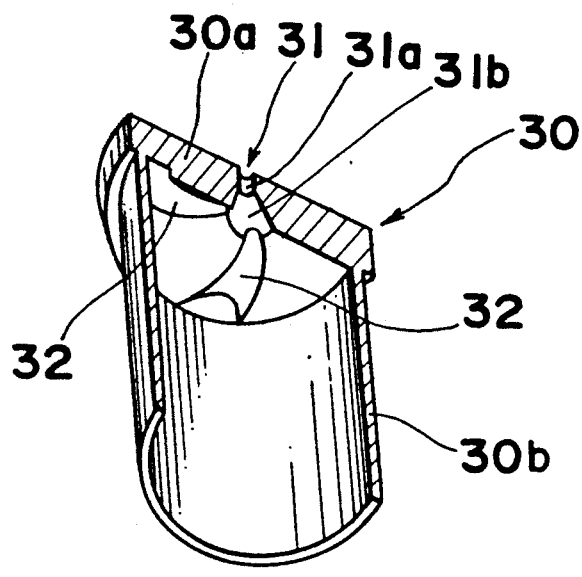
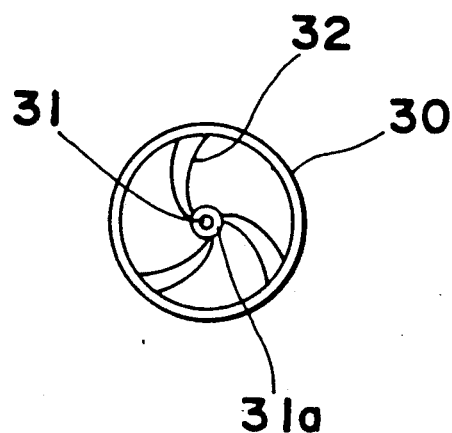

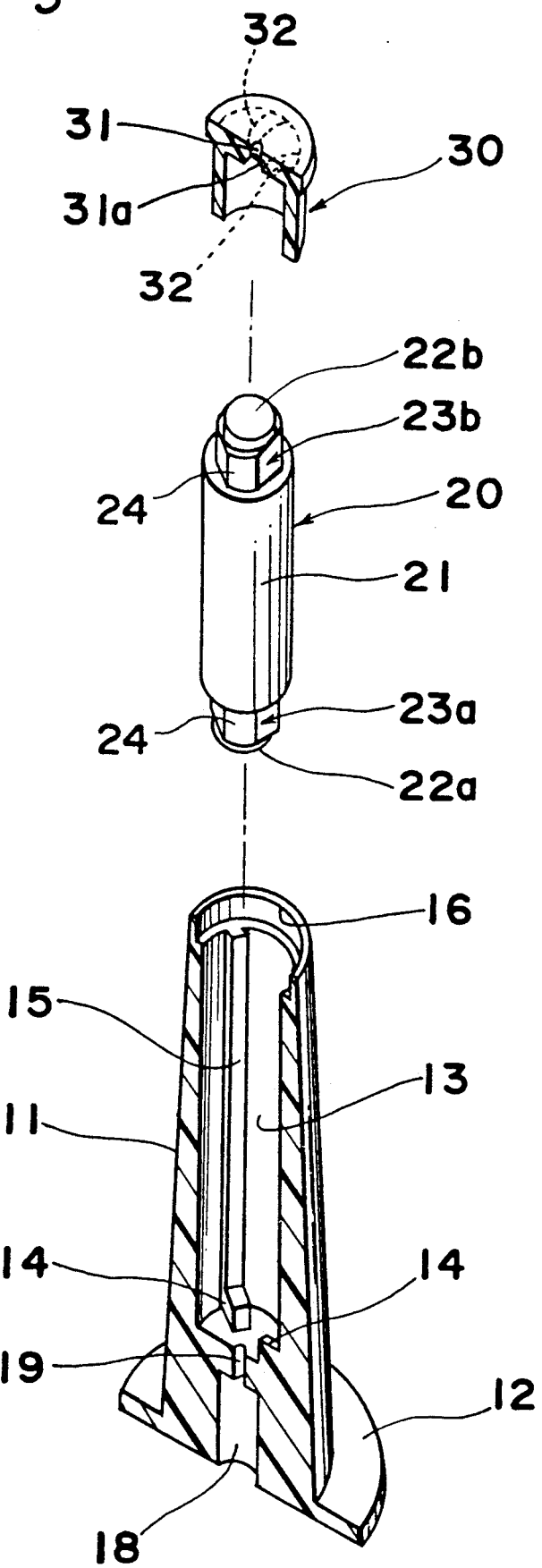

DISPOSABLE NOZZLE ADAPTER FOR INTRANASAL SPRAY CONTAINERS

BACKGROUND OF THE INVENTION

1. Field of the Invention

The present invention relates to a disposable nozzle adapter for intranasal spray containers and, more particularly, to a disposable spray nozzle adapter for intranasally spraying a viscous medical solution in combination with a spray container.

2. Description of the Prior Art

In the treatment of rhinitis, medical sprayers or spray containers have widely been used to administer medical solutions to nasal cavities. Since medical substances are absorbed easily through nasal mucous membranes, the intranasal administration of medical substances has attracted much interest recently for the purpose of systemic treatment.

The sprayers or spray containers of the prior art generally comprise a pressurized container or a container with a manually-operated pump, and a spray nozzle fixed to the container. If such a spray container is applied for intranasal administration, especially for collective administration of medical substances such as, for example, influenza HA vaccine, it is required to use the same spray container for a number of people as the container is filled with a medical solution several times the required quantity for a dose. This makes a unfavorable impression on the person to be intranasally administered and causes a danger of infection of diseases if any one of the group has an infectious diseases such as acquired immune deficiency syndrome (AIDS).

An easy solution for these problems is to wipe or disinfect the nozzle of the container with a disinfectant each time. However, such an operation is troublesome and leaves the problem of a unfavorable impression unsolved.

It may be a good solution to use a removable spray nozzle in combination with a spray container, as disclosed for example, in lying-open Japanese patent No. 60-85759 (corresponding to U.S. Pat. No. 4,801,093). This spray nozzle comprises a top-closed cylindrical external member with a central channel, and a substantially cylindrical internal member arranged in the central channel of the external member to form a passage, said external member having a spray opening formed in the top wall of the external member and communicated with the central channel through one or more grooves carved on the inner surface of the top wall and through a cavity surrounding the spray opening.

In use, the spray nozzle is fitted on a valve stem of the spray container with a manually operated pump to complete the spray unit, and a medical solution in the container is sprayed through the spray opening by operating the pump.

This spray unit provides an excellent spraying action for a medical solution with a relatively low viscosity, but it is impossible to spray viscous medical solutions in finely divided particles. For example, if the spray unit is used for intranasal administration of medical solutions having a viscosity of 500 to 3000 cps, the solution is never sprayed in finely divided particles, but is ejected linearly like a jet because of its high viscosity. Thus, if the solution is ejected when the person breathes in, the solution would be sucked into the trachea and, worst of all, into the lungs.

SUMMARY OF THE INVENTION

It is therefore an object of the present invention to provide a disposable nozzle adapter for intranasal spray containers, which makes it possible to spray viscous medical solutions into nasal cavities in finely divided particles of 20 to 100 $\mu$m at a wide spraying angle.

Another object of the present invention is to provide a disposable nozzle adapter for intranasal spray containers, which is easy to manufacture and simple to handle.

These and other objects of the present invention are solved by providing a disposable nozzle adapter for intranasal administration of a viscous medical solution in combination with a spray container, which comprises;

a cylindrical body having at its one end a cylindrical chamber and at the other end a central bore for attachment of said spray container, said bore being communicated with said chamber through a channel;

a rod provided on its one end at the least with a small-sized portion and middle-sized portion and arranged in the chamber of said body to form at least one channel between its external surface and the inner surface of said chamber; and a nozzle tip having a top wall and a cylindrical portion extending therefrom, said top wall being provided with a central spray opening including a tapered recess, and swirl grooves extending from said tapered recess to the inner surface of said cylindrical portion, said swirl grooves having a cross-sectional area increasing outwardly, the cross-sectional area of said swirl groove being 0.03 to 0.08 mm$^2$ at the minimum, said nozzle tip being fitted in the opening of said chamber and engaged with the middle-sized portion of said rod to form an annular channel surrounding said small-sized portion and being communicated with said grooves.

Particularly, the disposable nozzle adapter of the present invention is suitable for administration of viscous medical solutions with a viscosity of 500 to 3000 cps and, especially, those containing at least one carboxyvinyl polymer as a thickening agent and/or dispersion stabilizer and having a viscosity ranging from 500 to 3000 cps. It is preferred that the spray opening of the nozzle tip has a diameter ranging from 0.2 to 0.4 mm.

In one preferred embodiment, the adapter body is provided on its inner wall with longitudinally extending plural ribs which extend in parallel with the center axis of the body to form channels for the solution between its inner surface and the rod arranged therein.

In the present invention, the viscous medical solution ejected into the adapter is accelerated while passing though the swirl grooves, whirled in its tapered recess of the spray opening and then sprayed in finely divided particles with a diameter of 20 to 100 $\mu$m at a wide spraying angle. Thus, the disposable nozzle adapter according to the present invention makes it possible to spray the medical solution in finely divided particles even if the solution has a high viscosity ranging from 500 to 3000 cps.

Since the nozzle adapter of the present invention is removably fitted on the nozzle of the spray container, the adapter can be replaced with a new one each time, thus making it possible to prevent the infection with diseases even when the intranasal spray unit is applied for collective administration of viscous medical solutions such as influenza HA vaccine.

The invention will be further apparent from the following description with reference to the accompanying drawings which show, by way of example only, one preferred embodiment thereof.

BRIEF EXPLANATION OF THE DRAWINGS

FIG. 1 is a side view of a medial spray unit with a disposable nozzle adapter embodying the present invention;

FIG. 2 is a partial section view of a medical spray unit shown in FIG. 1;

FIG. 3 is an exploded perspective view of a disposable nozzle adapter shown in FIG. 1;

FIG. 4 is an enlarged perspective section view of a nozzle tip shown in FIG. 3; and FIG. 5 is a bottom view of a nozzle tip shown in FIG. 2.

PREFERRED EMBODIMENTS OF THE INVENTION

Referring to the drawings, there is shown an intranasal spray unit comprising a spray container 1 with a nozzle 2, and a disposable nozzle adapter 10 removably fitted on the nozzle of the container 1. The spray container 1 is of a well-known type and has a manually-operated pumping means (not shown) to discharge a viscous medical solution 3 contained therein.

The viscous medical solution is incorporated with a carboxyvinyl polymer as a thickening agent and/or a dispersion stabilizer so that it has a viscosity ranging from 500 to 3000 cps.

The spray nozzle adapter 10 comprises an adapter body 11, a rod 20 arranged in a cylindrical chamber 13 of the body 11 and a spray nozzle tip 30 fitted in the top of the chamber 13.

The adapter body 11 has a cylindrical shape capable of being inserted into nasal cavities, and is provided at its lower end with a flange 12. The adapter body may have any other configurations, provided that it can be inserted into nasal cavities. The cylindrical chamber 13 has, at its top portion, a widened opening 16 for attachment of the nozzle tip 30. The body 11 has a bottom provided with a central bore 18 communicated with the chamber 13 through a passage 19 formed in the bottom wall for the chamber 13. The interior wall of the chamber 13 is provided with longitudinally extending plural ribs 15 (in this embodiment three ribs are provided) which extend in parallel with the center axis of the body and which are arranged at an angle of about 120° to one another to prevent the rod 20 from shaking or displacement as well as to form channels for the solution. As best shown in FIG. 3, the ribs 15 extends from the top end of the interior wall of the chamber 13 to the bottom where the ribs 15 are connected with projections 14, respectively.

The rod 20 is provided at both its ends with a middle-sized portion 23*a*, 23*b* and a small-sized portion 22*a*, 22*b* coaxially extending therefrom. Each middle-sized portion 23*a*, 23*b* is partially cut away to form projections 24 with a circular arc cross section as well as to form channels for the medical solution. The small-sized portion 22*a* is placed on the projections 14.

The rod 20 is so designed that the outside diameter of the barrel 21 is equal to or slightly smaller than that of the diameter of a circle drawn around the projections 15, while the diameter of the small sized portion 22*b* is smaller than that of the nozzle tip 30 to form an annular channel surrounding the small-sized portion.

The nozzle tip 30 is a top-closed cylindrical member with a flange. The flange is fitted in the widened opening 16 of the body 11 and placed on the stepped portion 17 of the body 11. The nozzle tip 30 is provided at its top wall 30*a* with a spraying opening 31 composed of a straight portion 31*a* and a tapered recess 31*b*, as best shown in FIG. 4. The straight portion 31*a* of the spray opening 31 has a diameter ranging from 0.2 to 0.4 mm and a length of 0.2 mm. The tapered portion 31*b* extends downwardly from the lower end of the straight portion 31*a* at an opening angle of 86 to 126° and is communicated with three swirl grooves 32 carved on the bottom surface of the top wall 30*a*. The cylindrical portions 30*b* of the nozzle tip 30 are so designed that they have a diameter substantially equal to the outer diameter of the middle-sized portion 23*b*. Thus, the nozzle tip 30 can be fixed to the rod 20 by press-fitting its cylindrical portion 30*b* on the projections 24.

The swirl grooves 32 have a semicircular or semi-elliptical cross section gradually increasing outwardly. The grooves have a width of 0.15 to 0.4 mm and a depth of 0.15 to 0.25 mm at the portion where it is communicated with the tapered portion 31*b*. The size of the grooves is so determined that each groove has the minimum cross sectional area of 0.03 to 0.08 $mm^2$. If the cross sectional area is less than 0.03 $mm^2$, it is difficult to spray the viscous medical solution as the flow rate of the solution is considerably decreased. In addition, there is a danger that the grooves are stopped up during operation. If the cross sectional area of the groove exceeds 0.08 $mm^2$, the medical solution is not atomized into finely divided particles.

In use, the nozzle adapter 10 is held, for example, with the middle and index fingers so as to hook these fingers around the flange 12 and then inserted into nasal cavity. Then, the container 1 is pushed by the thumb to allow the container 1 to slide along its nozzle 2 toward the flange 12 of the adapter 10. The medical solution in the container 1 is forced into the nozzle adapter 10 through the passage 19, passes into the passage formed between the bottom of the chamber 13 and the rod 20, passages formed between the rod 20 and the internal surface of the body 11 and partitioned by the ribs 15, enters into the annular channel surrounding the small-sized portion 22*b* of the rod 20, and flows into the spraying opening through the swirl grooves. During passing though the swirl grooves, the solution is accelerated because of the decrease in the cross sectional area of the grooves, whirled in the tapered recess 31*b* of the spray opening, and then sprayed through the straight portion of the opening 31.

In that manner, the spray container may be used several times by replacing the nozzle adapter with a new one for every spraying, provided that the spray container is filled with a viscous medical solution several times the required quantity for a dose.

In fact, the medicinal solution containing a carboxyvinyl polymer and having a viscosity of 500 to 3000 cps was sprayed in finely divided particles with particle sizes of 20 to 100 $\mu m$.

In the above embodiment, a tapered cylindrical hollow member is used for the adapter body, but there is no restriction in shapes of the adapter body. The adapter body may take any desired shapes as occasion demands.

For example, the adapter body 11 can be modified so that it has a cylindrical portion extending from the periphery of the flange 12. Also, the adapter body 11 may have a pair of flanges extending diametrically from its lower end, instead of the annular flange 12. Further, the adapter body 11 may be provided at its barrel with two or more projections extending radially in diametrically opposed directions from each other to permit an operator to hook two fingers around the flanges as well as to allow for easy handling of the spray unit. In any case, the size and shape of spray nozzle may be determined optionally so as to adjust a spraying angle and size or size distribution of particles sprayed.

Since the rod has small-sized portions 22a, 22b with arch-shaped projections 23a, 22b, the rod may be loaded into the body in any directions, thus making it easy to assemble the adapter. However, the rod may have one small-sized portion 22a with an arch-shaped projections 24 on one side which interacts with the nozzle tip 30.

WHAT IS CLAIMED IS

1. A disposable nozzle adapter for intranasal administration of a viscous medical solution in combination with a spray container, which comprises;
   a cylindrical body having at its one end a cylindrical chamber including an opening and at the other end a central bore for attachment of said spray container, said bore being communicated with said chamber through a passage;
   a rod provided on at least one of its ends with a small-sized portion and middle-sized portion and arranged in the chamber of said body to form at least one channel between its external surface and the inner surface of said chamber; and
   a nozzle tip having a top wall and a cylindrical portion extending therefrom, said top wall being provided with a central spray opening including a tapered recess, and swirl grooves extending from said tapered recess to the inner surface of said cylindrical portion, said swirl grooves having a minimum cross-sectional area of said tapered recess and increasing outwardly, the cross-sectional area of each of said swirl grooves being 0.03 to 0.08 $mm^2$ at the minimum, said nozzle tip being fitted in the opening of said chamber and engaged with the middle-sized portion of said rod to form an annular channel surrounding said small-sized portion and being communicated with said grooves.

2. A nozzle adapter according to claim 1 wherein said viscous medical solution has a viscosity ranging from 500 to 3000 cps.

3. A nozzle adapter according to claim 1 wherein said body is provided on its inner wall with longitudinally extending plural ribs which extend in parallel with the center axis of the body to form the at least one channel for the solution between said rod and the inner surface of said chamber.

4. A nozzle adapter according to claim 1 wherein said viscous medical solution contains at least one carboxyvinyl polymer and has a viscosity ranging from 500 to 3000 cps.

5. A nozzle adapter according to claim 1 wherein said spray opening of the nozzle tip has a diameter ranging from 0.2 to 0.4 mm.

* * * * *